United States Patent [19]

Aichinger et al.

[11] Patent Number: 5,910,603
[45] Date of Patent: *Jun. 8, 1999

[54] ESTERIFICATION OF (METH)ACRYLIC ACID WITH AN ALKANOL

[75] Inventors: Heinrich Aichinger, Mannheim; Matthias Geisendörfer, Neustadt; Holger Herbst, Frankenthal; Gerhard Nestler, Ludwigshafen, all of Germany

[73] Assignee: BASF Aktiengesellschaft, Ludwigshafen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/701,989

[22] Filed: Aug. 23, 1996

[30] Foreign Application Priority Data

Sep. 28, 1995 [DE] Germany .............................. 195 36 191

[51] Int. Cl.⁶ .................................................... C07C 69/52
[52] U.S. Cl. ............................................................ 560/205
[58] Field of Search .............................................. 560/205

[56] References Cited

FOREIGN PATENT DOCUMENTS

| 1 058 390 | 2/1992 | China . |
| 1 063 678 | 8/1992 | China . |
| 2 339 519 | 2/1974 | Germany . |
| 195 47 485 | 5/1996 | Germany . |
| 47-15936 | 5/1972 | Japan . |
| 57-62229 | 4/1982 | Japan . |
| 5 25086 | 2/1993 | Japan . |
| 6 65149 | 3/1994 | Japan . |
| 923 595 | 4/1963 | United Kingdom . |

OTHER PUBLICATIONS

Ullmann's Encyclopedia of Industrial Chemistry, vol. A1, "Abrasives to Aluminum Oxide", 5$^{th}$ Edition, pp. 167–169, 1985.

Derwent abstract 96–231836; abstract of DE 195447485, May 1996.

*Primary Examiner*—Samuel Barts
*Attorney, Agent, or Firm*—Oblon, Spivak, McClelland, Maier & Neustadt, P.C.

[57] ABSTRACT

In a process for esterifying (meth)acrylic acid with an alkanol in the presence of an acidic esterification catalyst, in which unconverted starting compounds and the (meth) acrylates to be formed are separated off by distillation and an oxyester-containing bottom product is formed, the bottom product is separated off and is heated in the presence of an acid to 150–250° C. and the pressure is adjusted so that the cleavage products formed under the abovementioned conditions from the oxyesters contained in the bottom product evaporate directly. The process can be carried out in the presence of molecular oxygen. Mineral acids, for example sulfuric acid or phosphoric acid and/or alkanesulfonic or arylsulfonic acids, for example methanesulfonic acid or p-toluenesulfonic acid, can be added to the bottom product.

24 Claims, No Drawings

ESTERIFICATION OF (METH)ACRYLIC ACID WITH AN ALKANOL

The present invention relates to a process for esterifying (meth)acrylic acid with an alkanol in the presence of an esterification catalyst, in which unconverted starting compounds and the (meth)acrylate to be formed are separated off by distillation, and an oxyester-containing bottom product is formed. The term (meth)acrylic acid denotes in a known manner acrylic or methacrylic acid.

Alkyl esters of (meth)acrylic acid are usually prepared by esterifying (meth)acrylic acid with alkanols at elevated temperatures in the liquid phase in the presence or absence of a solvent and in the presence of an acid as a catalyst (DE-A 23 39 519). The disadvantage of this method of preparation is that, as secondary reactions under the abovementioned esterification conditions, unconverted starting alcohol undergoes a Michael addition reaction at the double bond of the resulting alkyl (meth)acrylate with formation of a compound of the general formula I below, and unconverted (meth)acrylic acid undergoes said addition reaction with formation of a compound of the general formula II. Multiple addition is also possible. Furthermore, mixed types may occur. These adducts (alkoxyesters and acyloxyesters) are referred to as oxyesters for short.

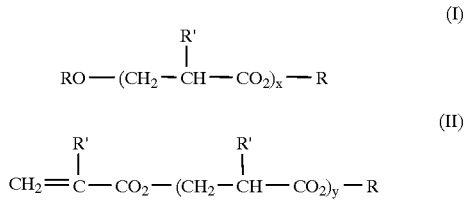

where x and y are each 1–5, R is alkyl and R' is H or $CH_3$

If R' is H, the esterification in question is that of acrylic acid; if R' is $CH_3$, the esterification in question is that of methacrylic acid.

In the preparation of esters of acrylic acid, the problem of oxyester formation is particularly acute, the oxyesters mainly formed are the alkoxypropionic esters and the acyloxypropionic esters where x and y are each 1. In the preparation of esters of methacrylic acid, the oxyester formation takes place to a lesser extent. The formation of oxyesters is described in DE-A 23 39 529. This states that the formation of oxyesters is essentially independent of the specific esterification conditions. Of very particular importance is the oxyester formation in the preparation of acrylates of $C_1$–$C_8$-alkanols, in particular of $C_4$–$C_8$-alkanols, very particularly in the preparation of n-butyl acrylate and 2-ethylhexyl acrylate.

Typical for the oxyesters is that their boiling point is above the boiling points of starting acid, starting alcohol, target ester formed and any organic solvent present.

Any desired esterification reaction mixture is usually worked up by separating unconverted starting compounds and the target ester from the reaction mixture by distillation, the acid catalyst used for the esterification being separated off beforehand, if required, by extraction by means of water and/or aqueous alkali (cf. for example Ullmann's Encylopedia of Industrial Chemistry, Vol. A1, 5th Ed. VCH, page 167 et seq.). The bottom product remaining as a result of such a working up by distillation contains the oxyesters, which give rise to considerable loss of yield.

Various other processes have therefore been investigated in order to solve the problems arising from the occurrence of the oxyesters. Thus, JP-A-82/62229 describes the alkaline hydrolysis of the high-boiling esterification residue. A part of the alcohol used and acrylic acid and β-hydroxypropionic acid or salts thereof are recovered in this manner. A simple and economical recycling of the products to the esterification reaction is therefore not possible. Japanese Published Application 72/15936 describes the preparation of acrylates by reacting β-alkoxypropionic esters with acrylic acid in the presence of strong acids (transesterification). However, equimolar amounts of β-alkoxypropionic acid are obtained as a byproduct and cannot be recycled to the esterification reaction and therefore constitute waste. JP-A-93/25086 describes the cleavage of the Michael adduct butyl β-butoxypropionate (cf. formula I, x=1, R=butyl) at elevated temperatures and in the presence of sulfuric acid and of an excess of water. However, the conversion is only about 30%. Finally, JP-A-94/65149 describes the cleavage of the Michael adducts I and II (see above, x=y=1) in the presence of titanium alcoholates. Here, the conversion is likewise low (<60%) and large amounts of titanate are required. This process is therefore uneconomical and, owing to the large amounts of titanate to be disposed of, causes environmental pollution.

GB 923 595 describes the recovery of monomers from the residue of the esterification of acrylic acid with alkanols in the absence of molecular oxygen. Inter alia, the removal of all volatile monomers prior to the cleavage, cleavage in the presence of sulfuric acid and the removal of the cleavage products with the aid of an inert gas stream are recommended. According to the Examples, the cleavage is always carried out at not less than 300° C. Coke is formed as a residue (17–40%). This has to be removed from the reactor by a procedure resembling mining. This process is therefore neither economical nor feasible on an industrial scale. A further disadvantage is the required exclusion of oxygen.

CN-A 1,063,678 describes the cleavage of the alkoxypropionic ester contained in the esterification residue, in the presence of sulfuric acid, in a cascade, the temperature and catalyst concentration (0.8–1.5%) differing in each reactor. Coupled to the cleavage is a distillation for the separation of alkanol and acrylate. The process is very inconvenient and does not give high conversions.

Finally, CN-A 105 8390 describes the cleavage of alkoxypropionic esters in the presence of sulfuric acid, etc. into alkanols and acrylates. This is a stepwise procedure. First, the cleavage is carried out under reflux and then the reaction products are distilled off. The cleavage of the acrylate-containing ester residues of the ethyl/methyl acrylate preparation (ethyl ethoxypropionate, methyl methoxypropionate) is carried out in the presence of ethanol and methanol, respectively. Here too, the process is complicated and does not give high conversions.

It is an object of the present invention to carry out the recleavage of the oxyesters contained in this bottom product and the further use of the resulting starting acid, starting alcohol and target ester in the esterification without the disadvantages of the prior art processes.

We have found that this object is achieved, according to the invention, if the bottom product is separated off and the oxyesters contained therein are heated in the presence of an acid to 150–250° C. and the pressure is adjusted so that the cleavage products obtained under the abovementioned conditions from the oxyesters contained in the bottom product evaporate. In an advantageous embodiment of the invention, the process is carried out in the presence of molecular oxygen.

In an advantageous development of the invention, further acids, for example mineral acids, such as sulfuric acid or phosphoric acid, and/or organic acids, such as alkanesulfonic or arylsulfonic acids, for example methanesulfonic or p-toluenesulfonic acid, are added to the bottom product in addition to the acidic esterification catalyst which may already be present. The total amount of acid then present may be from 1 to 20, preferably from 5 to 15,% by weight, based on the amounts of the bottom product. It is particularly advantageous if a stripping gas which preferably contains molecular oxygen is passed through the bottom product as an entraining agent for the cleavage products. Advantageously, air or a mixture of air with an inert gas (eg. nitrogen) is used as the stripping gas.

A simple heatable stirred reactor having a double-wall heating means or heating coil or a forced-circulation evaporator, for example a falling-film evaporator or flash evaporator, coupled to a dwell container, can be used for working up the oxyesters obtained as bottom product in the esterification. For better separation of the cleavage products, a rectification apparatus, for example a packed column or plate column, mounted on the cleavage apparatus may be advantageous. This rectification apparatus is, as a rule, stabilized with polymerization inhibitors (eg. phenothiazine, hydroquinone monomethyl ether, etc.) during operation.

The conditions for carrying out the novel process for the cleavage of the oxyesters obtained as bottom product in the esterification are the following:

| Catalyst: | at least one acid selected from the group consisting of mineral acids, eg., sulfuric acid and phosphoric acid, and organic acids, such as alkanesulfonic or arylsulfonic acids, for example methanesulfonic acid or p-toluenesulfonic acid |
| --- | --- |
| Amount of catalyst: | 1–20, preferably 5–15, % by weight, based on the amount of the bottom product |
| Temperature: | 150–250° C., preferably 180–230° C. |
| Pressure: | preferably atmospheric pressure or reduced pressure |
| Stripping gas, if required | Amount: 1–100 l/h l |
| Reaction time: | 1–10 hours |
| Conversion: | as a rule about 80% |

The reaction is carried out, for example, in such a way that the bottom product to be cleaved is removed continuously from the working up of the esterification mixture by distillation and is fed with the cleavage catalyst to the cleavage reactor. The reaction can also be carried out batchwise. Also possible is a semicontinuous reaction procedure in which the product to be cleaved is fed continuously to the cleavage reactor which contains the cleavage catalyst, and the bottom product is removed batchwise from the cleavage reactor only after the end of the cleavage. The cleavage products are separated off continuously by distillation.

The applicability of the cleavage process described is not restricted to a special nature of the esterification process in which the byproducts obtained are the oxyesters, ie. the adducts I and II. As a rule, the esters are prepared by the conventional processes (cf. Ullmann's Encyclopedia of Industrial Chemistry, Vol. A1, 5th Ed., VCH, page 167 et seq.).

A typical example of the conditions under which the esterification which precedes cleavage of the oxyesters can take place may be described briefly asfollows:

| Alcohol: (meth)acrylic acid | 1:0.7–1.2 (molar) |
| --- | --- |
| Catalyst: | Sulfuric acid or sulfonic acids |

-continued

| Amount of catalyst: | 0.1–10% by weight (preferably 0.5–5% by weight), based on starting materials |
| --- | --- |
| Stabilization: | 200–2000 ppm of phenothiazine (based on the weight of the starting materials) |
| Reaction temperature: | 80–160° C., preferably 90–130° C. |
| Reaction time: | 1–10, preferably 1–6, hours |

If required, an entraining agent (eg. cyclohexane or toluene) is used for removing the water formed in the esterification. The esterification can be carried out under atmospheric, superatmospheric or reduced pressure, both continuously and batchwise.

In the acid-catalyzed esterification of acrylic acid with alkanols, the bottom product resulting after the acidic esterification catalyst, the unconverted starting materials and the acrylate have been separated off generally has the following composition:

1–20% by weight of acrylate

50–80% by weight of alkoxypropionates (cf. formula I)

5–30% by weight of acyloxypropionates (cf. formula II)

Remainder: mainly stabilizers (phenothiazine) and polymers

Further details and advantages of the novel process are stated in the Examples described below.

EXAMPLE 1

A circulation reactor (volume: 1 l) which consists of glass and is heated by means of a heating element was filled with 40 g of p-toluenesulfonic acid and 500 g of an esterification residue in the preparation of n-butyl acrylate, which residue has been freed from the acidic esterification catalyst. The residue contained 10.1% by weight of butyl acrylate, 65.4% by weight of butoxyester I and 20.0% by weight of acyloxyester II (R=$C_4H_9$). The remainder consisted of polymers, oligomers and polymerization inhibitor (phenothiazine). The cleavage temperature was 195° C. and the working pressure 1 atm.

Esterification residue was fed continuously to the cleavage reactor during the cleavage, with level control.

The cleavage products were removed in vapor form and condensed. An empty column (50 cm×2.8 cm) was present as a splashguard between reactor and condenser. 1589 g of esterification residue were fed to the cleavage in the course of 21.5 hours in this manner. According to the gas chromatographic analysis, the resulting condensate (1278 g) contained:

69.1% by weight of butyl acrylate 18.3% by weight of butanol 6.5% by weight of acrylic acid 7.0% by weight of olefins and ethers 3.5% by weight of butyl butoxypropionate Conversion: 84% by weight, based on oxyester.

EXAMPLE 2

A cleavage apparatus consisting of a 1 l stirred reactor, an attached column (30 cm×2.8 cm, 5 mm Raschig rings) and a condenser was filled with 15 g of p-toluenesulfonic acid and 500 g of a bottom liquid which was obtained in the preparation of 2-ethylhexyl acrylate, no longer contained any acidic esterification catalyst and had the following composition:

65.0% by weight of alkoxyester I (R=$C_8H_{17}$)

5.5% by weight of acyloxyester II (R=$C_8H_{17}$)

2.1% by weight of 2-ethylhexyl acrylate 1.0% by weight of di-2-ethylhexyl ether

Remainder: polymers, oligomers, polymerization inhibitor (phenothiazine)

The cleavage temperature was 215° C. and the working pressure 1 atm. During the cleavage, 100 l/h of air were passed through continuously as a stripping gas. The reaction time was 1.5 hours. According to gas chromatographic analysis, the condensate (288 g) contained:

7.2% by weight of acrylic acid 25.5% by weight of 2-ethylhexanol 53.0% by weight of 2-ethylhexyl acrylate 1.9% by weight of di-2-ethylhexyl ether 12.2% by weight of octenes <1% by weight of alkoxyester I (R=$C_8H_{17}$)

Conversion: 79% by weight, based on oxyester

EXAMPLE 3

A cleavage apparatus consisting of a 1 l stirred reactor, an attached column (30 cm×2.8 cm, 5 mm Raschig rings) and a condenser was filled with 25 g of p-toluenesulfonic acid and 500 g of a bottom liquid which was obtained in the preparation of 2-ethylhexyl acrylate, no longer contained any acidic esterification catalyst and had the following composition:

65.0% by weight of alkoxyester I (R=$C_8H_{17}$)

5.5% by weight of acyloxyester II (R=$C_8H_{17}$)

2.1% by weight of 2-ethylhexyl acrylate 1.0% by weight of di-2-ethylhexyl ether

Remainder: polymers, oligomers, esterification stabilizer (phenothiazine)

The cleavage temperature was 190° C. at 50 mbar. According to gas chromatographic analysis, the condensate (321 g) contained:

4.2% by weight of acrylic acid 27.9% by weight of 2-ethylhexanol 52.2% by weight of 2-ethylhexyl acrylate 2.7% by weight of di-2-ethylhexyl ether 15.5% by weight of octenes <1% by weight of alkoxyester I (R=$C_8H_{17}$)

Conversion: 88% by weight, based on oxyester

The Examples show that conversions of about 80% by weight or more in the recleavage can be achieved by the novel process.

We claim:

1. A process comprising:
   1) esterifying (meth)acrylic acid with an alkanol in the presence of an acidic esterification catalyst,
   2) separating unconverted starting compounds, a (meth)acrylate and an oxyester-containing bottom product by distillation;
   3) heating a composition consisting essentially of said oxyester-containing bottom product and an acid, to from 150–250° C. at a pressure such that cleavage products formed from oxyesters contained in said bottom product are isolated concurrent with cleavage.

2. A process as claimed in claim 1, which is carried out in the presence of molecular oxygen.

3. A process as claimed in claim 1, wherein a mineral acid, for example sulfuric acid or phosphoric acid, or an alkanesulfonic acid or arylsulfonic acid, for example methanesulfonic acid or p-toluenesulfonic acid, is added to the bottom product.

4. A process as claimed in claim 1, wherein the amount of acid present is from 1 to 20, preferably from 5 to 15,% by weight, based on the amount of bottom product.

5. A process as claimed in claim 1, wherein reduced pressure (<1 atm) is used in the cleavage.

6. A process as claimed in claim 1, wherein a stripping gas is passed through the bottom product, as an entraining agent for the cleavage products.

7. A process as claimed in claim 6, wherein the stripping gas used is an oxygen-containing gas.

8. A process as claimed in claim 1, wherein the cleavage products obtained are recycled directly to the esterification.

9. A process as claimed in claim 1, wherein the bottom product is the bottom product formed in the esterification of n-butanol or 2-ethylhexanol.

10. A process as claimed in claim 3, wherein a stripping gas is passed through the bottom product, as an entraining agent for the cleavage products and/or the stripping gas used is an oxygen-containing gas and/or the cleavage products obtained are recycled directly to the esterification.

11. A process comprising:
   1) esterifying (meth)acrylic acid with an alkanol in the presence of an acidic esterification catalyst,
   2) separating unconverted starting compounds, a (meth)acrylate and an oxyester-containing bottom product by distillation;
   3) heating a composition comprising said oxyester-containing bottom product and an acid, to from 180–250° C. at a pressure such that cleavage products formed from oxyesters contained in said bottom product are isolated concurrent with cleavage.

12. The process as claimed in claim 11, which is carried out in the presence of molecular oxygen.

13. The process as claimed in claim 11, wherein said acid is selected from the group consisting of a mineral acid, an alkanesulfonic acid, an arylsulfonic acid and a mixture thereof.

14. The process as claimed in claim 11, wherein said acid is selected from the group consisting of sulfuric acid, phosphoric acid, methanesulfonic acid, p-toluenesulfonic acid and a mixture thereof.

15. The process as claimed in claim 11, wherein the amount of acid present is from 1 to 20% by weight based on the amount of bottom product.

16. The process as claimed in claim 11, wherein the amount of acid present is from 5 to 15% by weight based on the amount of bottom product.

17. The process as claimed in claim 11, wherein reduced pressure (<1 atm) is used in the cleavage.

18. The process as claimed in claim 11, wherein a stripping gas is passed through the bottom product, as an entraining agent for the cleavage products.

19. The process as claimed in claim 18, wherein said stripping gas used is an oxygen-containing gas.

20. The process as claimed in claim 11, wherein the cleavage products obtained are recycled directly to the esterification.

21. The process as claimed in claim 11, wherein the bottom product is the bottom product formed in the esterification of n-butanol or 2-ethylhexanol.

22. The process of claim 13, wherein a stripping gas is passed through the bottom product, as an entraining agent for the cleavage products and/or the stripping gas used is an oxygen-containing gas and/or the cleavage products obtained are recycled directly to the esterification.

23. The process of claim 1, further comprising isolating said cleavage products.

24. The process of claim 11, further comprising isolating said cleavage products.

* * * * *